US00PP35557P3

(12) United States Plant Patent
Alcock

(10) Patent No.: US PP35,557 P3
(45) Date of Patent: Dec. 26, 2023

(54) ***COPROSMA* PLANT NAMED 'ALDAWN'**

(50) Latin Name: *Coprosma repens*
Varietal Denomination: ALDAWN

(71) Applicant: Neil Alcock, Caernarfon (GB)

(72) Inventor: Neil Alcock, Caernarfon (GB)

( * ) Notice: Subject to any disclaimer, the term of this patent is extended or adjusted under 35 U.S.C. 154(b) by 0 days.

(21) Appl. No.: 18/101,417

(22) Filed: Jan. 25, 2023

(65) Prior Publication Data

US 2023/0292640 P1 Sep. 14, 2023

(30) Foreign Application Priority Data

Mar. 12, 2022 (QZ) ..... PBR 20220668

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00
See application file for complete search history.

(56) References Cited

PUBLICATIONS https://twitter.com/NeilAlcock/status/1307954238941790208?lang=en (Screenshot); Sep. 21, 2020; 1 page.*
https://www.genesis-plantmarketing.co.uk/plant-brochure/?plant_id=4878; May 16, 2023; 3 pages.*

* cited by examiner

*Primary Examiner* — Kent L Bell
(74) *Attorney, Agent, or Firm* — Penny J Aguirre

(57) ABSTRACT

A new cultivar of *Coprosma* plant named 'ALDAWN' that is characterized by its variegated foliage dark purple-green centers and margins that are vibrant pink in late summer and fall with cool temperatures.

3 Drawing Sheets

Genus/species: *Coprosma repens*.
Varietal denomination: 'ALDAWN'.

CROSS-REFERENCE TO A RELATED APPLICATION

This application claims priority to European Community Plant Variety Office (CPVO) Plant Breeder's Rights Application No. 2022/0668 filed on Mar. 12, 2022, under 35 U.S.C. 119(f), the entire contents of which is incorporated by reference herein.

BACKGROUND OF THE INVENTION

The present invention relates to a new and distinct cultivar of *Coprosma repens* and will be referred to hereafter by its cultivar name, 'ALDAWN'. 'ALDAWN' represents a new cultivar of evergreen shrub grown for landscape use.

The new cultivar was discovered by the Inventor in autumn of 2016 as a naturally occurring branch mutation of *Coprosma* 'Pacific Dawn' (not patented) in a trial field in Waunfawr, Gwynedd, United Kingdom.

Asexual propagation of the new cultivar was first accomplished by the Inventor by softwood stem cuttings in 2019 in Caernarfon, Gwynedd, The United Kingdom. Asexual propagation of the new cultivar by softwood stem cuttings has determined that the characteristics are stable and are reproduced true to type in successive generations.

SUMMARY OF THE INVENTION

The following traits have been repeatedly observed and represent the characteristics of the new *Coprosma*. These attributes in combination distinguish 'ALDAWN' as a unique cultivar of *Coprosma*.

1. 'ALDAWN' exhibits variegated foliage dark purple-green centers and margins that are vibrant pink when in late summer and fall with cool temperatures.

The parent plant of 'ALDAWN', differs from 'ALDAWN' in having foliage that is less intense in color. 'ALDAWN' can be most closely compared to the *Coprosma* cultivars 'Pacific Night' (not patented) and 'Fire Burst' (U.S. Plant Pat. No. 14,906). Both 'Pacific Night' and 'Fire Burst' are similar to 'ALDAWN' in having colored foliage. 'Pacific Night' differs from 'ALDAWN' in having foliage that is dark purple in color and a more narrow and upright plant habit. 'Fire Burst' differs from 'ALDAWN' in having foliage variegation that is purple and pink-red in color and a more rounded plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by Genesis Plant Marketing (the breeder's representative), Shoot Gardening, Worfield Plants, Kernock Park Plants, Gardeners Dream (and Amazon), Carbeth Plants, Grasslands, Twitter (by inventor) and GuiadeJardineria.

BRIEF DESCRIPTION OF THE DRAWINGS

The accompanying color photographs illustrate the overall appearance and distinct characteristics of the new *Coprosma*. The photographs In FIG. 1 and FIG. 2 were taken of a 2-year-old plant as grown in a greenhouse in a P-9 container in Caernarfon, Gwynedd, The United Kingdom.

The photograph in FIG. 1 provides a side view of the plant habit of 'ALDAWN' in summer.

Figure 1:
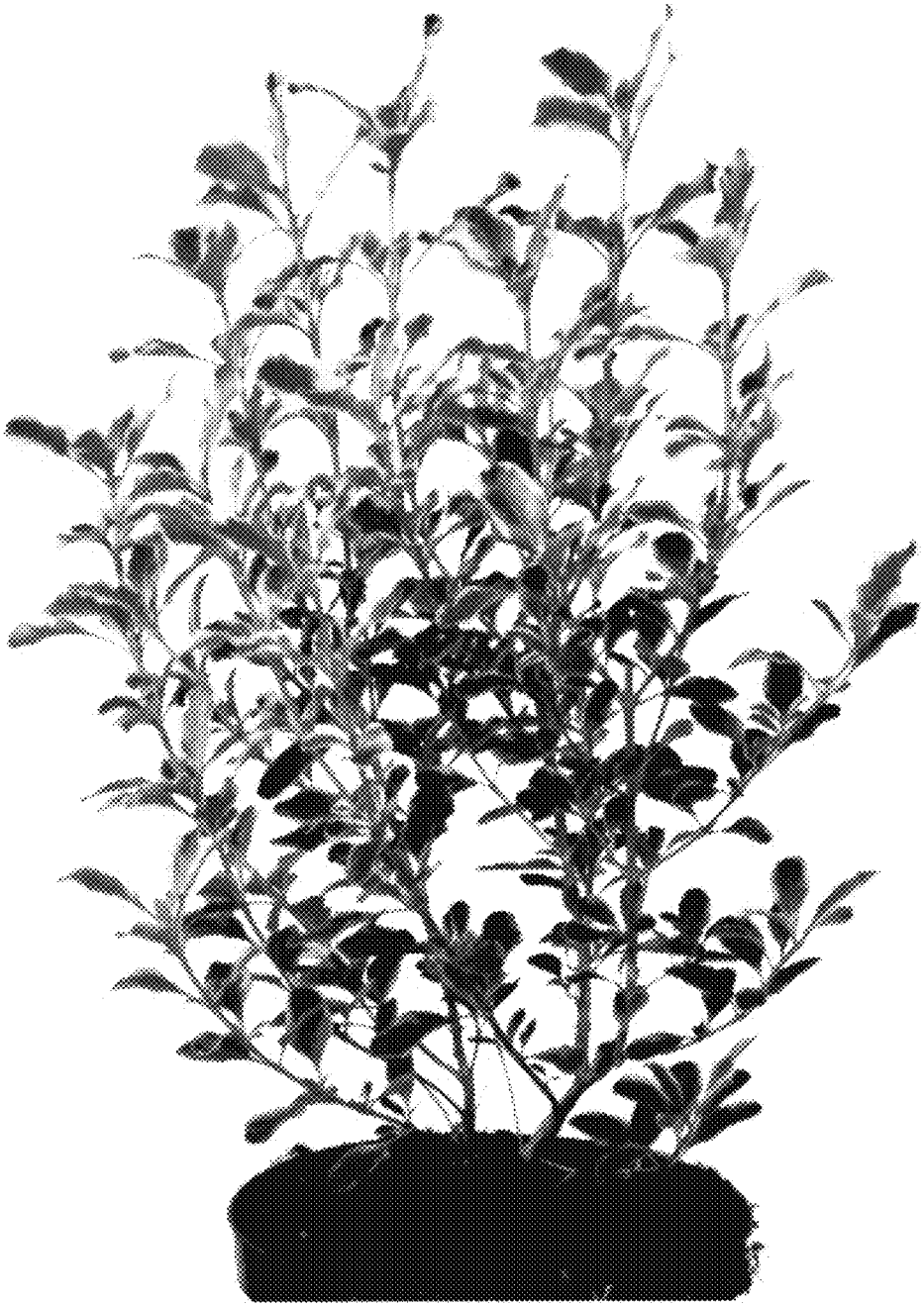
Figure 2:
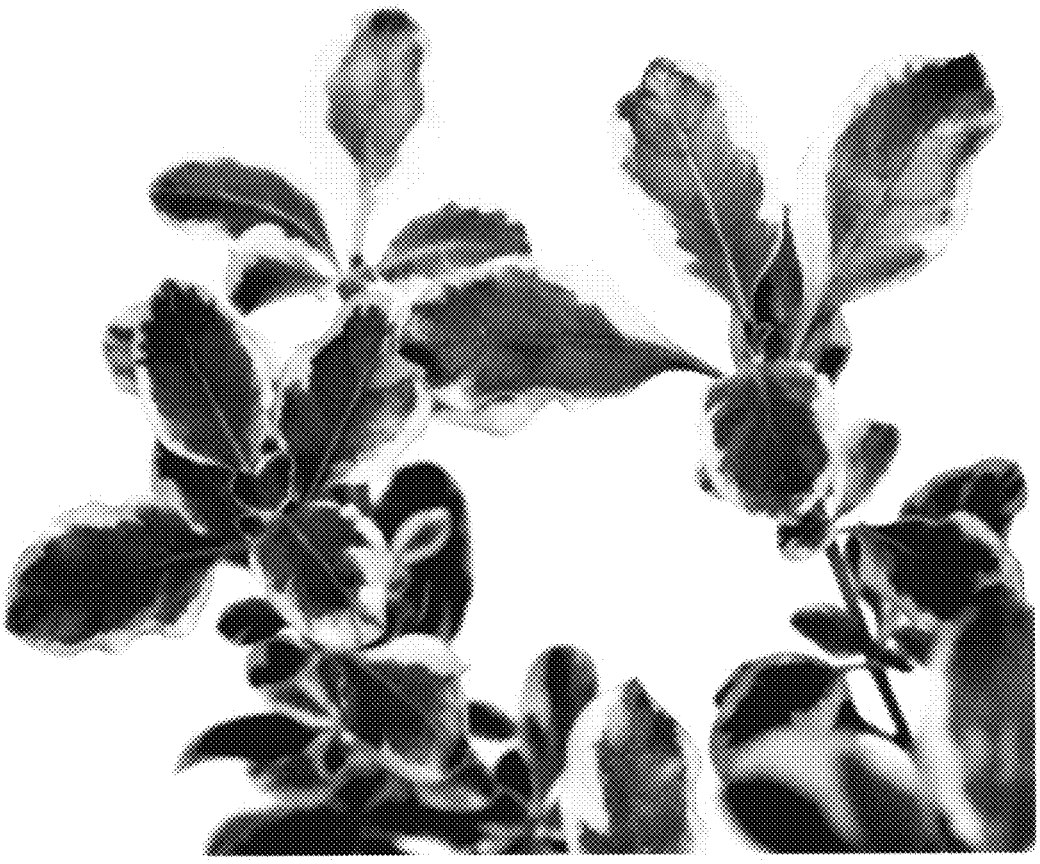

The photograph in FIG. 2 provides a close-up view of the foliage of 'ALDAWN' in summer.

Figure 3:
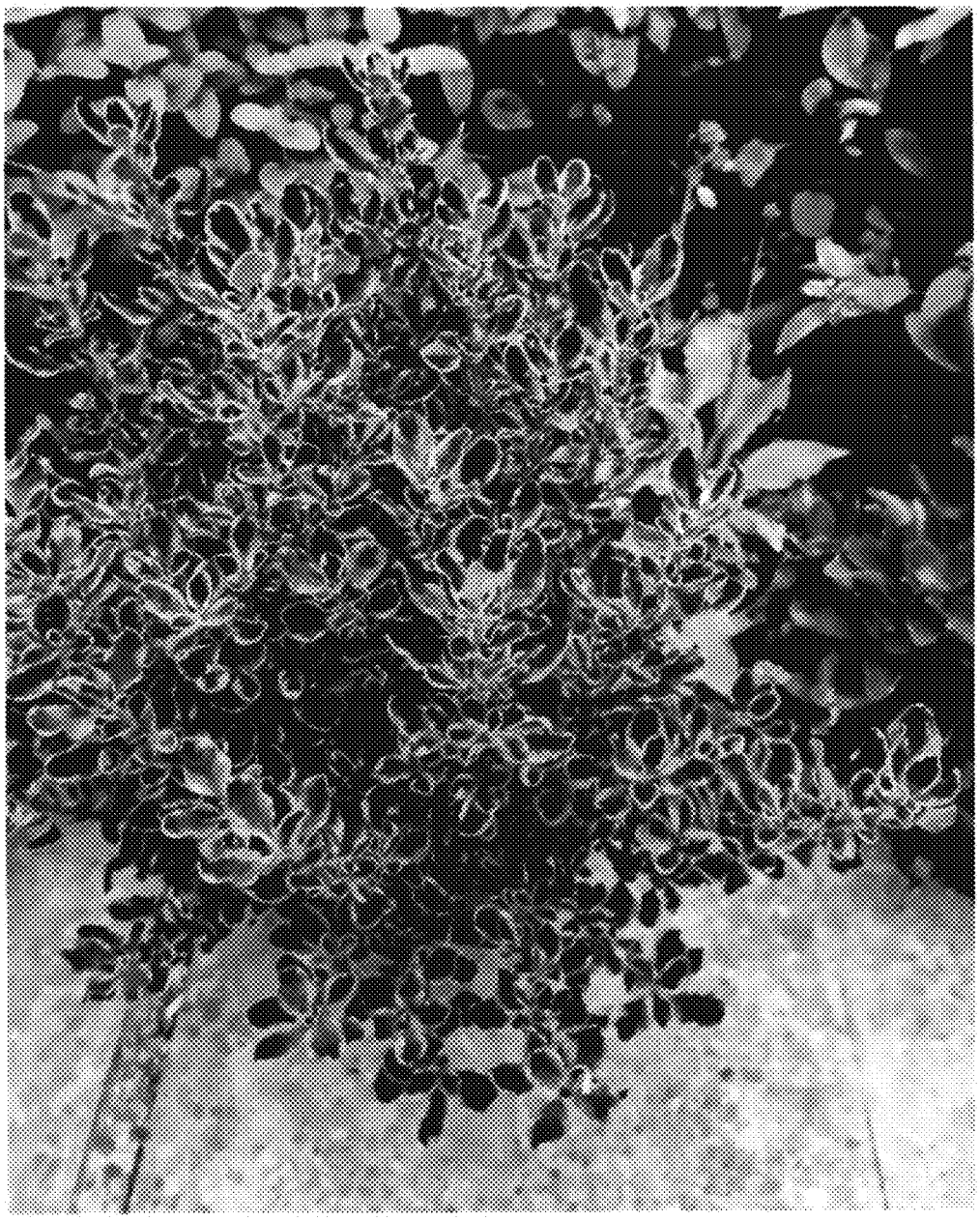

The Photograph in FIG. 3 was taken of a 2-year-old plant growing in a trial garden in Colchester, Essex, The United Kingdom and provides a view of the fall foliage of 'ALDAWN'.

The colors in the photographs are as close as possible with the photographic and printing technology utilized and the color values cited in the detailed botanical description accurately describe the colors of the new *Coprosma*.

BOTANICAL DESCRIPTION OF THE PLANT

The following is a detailed description of 2-year-old plants of the new cultivar as grown in a greenhouse in P-9 containers in Caernarfon, Gwynedd, The United Kingdom The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen shrub.

*Plant habit*.—Compact, broadly upright.

*Plant shape*.—Obovate.

*Height and spread*.—An average of 43 cm in height and 37 cm in spread as a 2-year-old plant as grown in a P-9 container.

*Hardiness*.—At least in U.S.D.A. Zones 8 to 10.

*Diseases and pest resistance*.—No susceptibility or resistance to diseases or pests has been observed.

*Root description*.—Fibrous and fine.

*Growth rate*.—Moderately vigorous.

*Propagation*.—Softwood stem cuttings.

*Root development*.—About 3 weeks to initiate roots and 10 weeks to produce a young plant from a rotted cutting.

Branch description:

*Branch color*.—Young; a blend of 152A and 199A, mature; a blend of 199A and 199B, internodes; 199B, tinged 182C, older stems and bark; 197A to 197C.

*Branch size*.—Up to 17 cm in length and 2 mm in diameter.

*Stem shape*.—Rounded.

*Stem quantity*.—An average of 2 main branches and 34 lateral branches per plant.

*Branch surface*.—Glossy, glabrous.

*Branch aspect*.—Main branch; vertical, lateral branch average angle of 50°.

*Branch habit*.—Main stems grow from base with lateral branches.

*Branch strength*.—Strong.

*Internode length*.—An average of 2.8 cm.

Foliage description:

*Leaf quantity*.—An average of 14 (7 pairs) per lateral branch.

*Leaf attachment*.—Petiolate.

*Leaf arrangement*.—Opposite.

*Leaf size*.—Average of 4 cm in length, 2.1 cm in width.

*Leaf shape*.—Broadly ovate to broadly oblong.

*Leaf base*.—Long acuminate.

*Leaf apex*.—Obtuse to broadly, bluntly acute.

*Leaf aspect*.—Flattened, average of 50° to lateral branch.

*Leaf venation*.—Pinnate, upper surface color; 152A, lower surface 178A.

*Leaf margin*.—Entire and undulate.

*Leaf surface*.—Both surfaces glossy and glabrous.

*Leaf color*.—Young upper surface; a blend of NN137B and 146A, occasionally flushed with 137C and 138A, irregularly broadly margined 6D, top tinged 35C, thin outside line along margin 35A, young lower surface; irregularly broadly margined 6D and 8C, top tinged 35C, thin outside line along margin 35A, mature upper surface; 147A, top tinged N199B, irregularly broadly margined 51A and 51B, thin outside line along margin 51A, mature lower surface; 138B, irregularly broadly margined 51C, thin outside line along margin 51A, in late summer and fall upper surface; a blend of N186A and N189A with margins N57C, in late summer and fall lower surface; N189C with margins N57D.

*Petioles*.—1.1 cm in length, average of 1.75 mm in width at the widest point, 1.25 mm in width at the narrowest point, strong, both surfaces are smooth, glabrous and glossy, upper surface color 152B, lower surface color 199A to 199B.

Flower description: Flowers have not been observed to date, flowers of the species are known to be absent or very insignificant and briefly present if produced.

It is claimed:

1. A new and distinct cultivar of *Coprosma* plant named 'ALDAWN' substantially as herein illustrated and described.

* * * * *